United States Patent [19]

Lin

[11] Patent Number: 4,554,374

[45] Date of Patent: Nov. 19, 1985

[54] PROCESS FOR DICARBONYLATION OF SIMPLE OLEFINS

[75] Inventor: Jiang-Jèn Lin, Round Rock, Tex.

[73] Assignee: Texaco Inc., White Plains, N.Y.

[21] Appl. No.: 644,416

[22] Filed: Aug. 27, 1984

[51] Int. Cl.$^4$ ............................................. C07C 67/38
[52] U.S. Cl. ................................... 560/204; 502/184; 502/185; 560/190
[58] Field of Search ................. 560/204; 502/184, 185

[56] References Cited

U.S. PATENT DOCUMENTS

| | | | |
|---|---|---|---|
| 3,397,225 | 8/1968 | Fenton | 560/207 |
| 3,397,226 | 8/1968 | Fenton | 560/204 |
| 3,755,421 | 8/1973 | Fenton et al. | 560/204 |
| 4,230,881 | 10/1980 | Romano et al. | 560/193 |
| 4,269,781 | 5/1981 | Vanderspurt et al. | 260/410.9 R |
| 4,281,173 | 7/1981 | Kesling | 560/204 |
| 4,281,174 | 7/1981 | Current | 560/204 |

Primary Examiner—Natalie Trousof
Assistant Examiner—Vera C. Clarke
Attorney, Agent, or Firm—Jack H. Park; Kenneth R. Priem; Cynthia L. Kendrick

[57] ABSTRACT

This invention relates to the carbonylation of olefins. More particularly it involves the carbonylation of aliphatic 1-olefins such as propylene and 1-octene to form for example, dimethyl α-methylsuccinate and dimethyl n-hexyl-succinate by a process comprising reacting said olefin with carbon monoxide and oxygen in the presence of a hetergeneous palladium catalyst, a copper-containing compound and a lithium-containing compound.

6 Claims, No Drawings ved by restricting both amounts of excess hydrogen ion and chloride ion.

U.S. Pat. No. 4, 281,174 discloses a catalyst system for preparing dimethyl oxalates by the oxidative carbonylation of alcohol which involves the reaction of CO, air and alcohol. Dimethyl carbonate can also be produced by a similar Pd catalyst.

In many processes known in the art separation of the high boiling aliphatic carboxylic acid or ester product from the catalyst system can be difficult. It would be advantageous to devise a catalyst system which is heterogenous, which improves the product distribution to desired carboxylic acid and which improves ease of product/catalyst separation. A supported (palladium-containing) catalyst system which allowed for easier separation of product from catalyst by filtration would be more efficient and far more attractive commercially. Furthermore, the selection of a suitable support for such a palladium catalyst system may be made so as to improve both the productivity to desired carboxylic acid/ester derivative and the selectivity to said desired product or products.

SUMMARY OF THE INVENTION

The present invention provides a process for the improved production of alkyl succinates by the oxidative carbonylation of 1-olefins with carbon monoxide and an alkanol in the presence of a catalyst comprising palladium on a suitable support in the presence of a copper-containing compound and a lithium-containing compound.

This invention demonstrates improved product selectivity, improved ratio of desired to undesired products, and improvement in ease, efficiency and commercial attractiveness of means of separation of product.

DESCRIPTION OF THE INVENTION

One or more objects of the present invention are accomplished by the process of the instant invention comprising reacting a 1-olefin, methanol and 2,2-dimethoxypropane (a dehydrating agent) with carbon monoxide and oxygen over a heterogenous, supported, palladium catalyst in the presence of a copper-containing compound and a lithium-containing compound in a reaction vessel and subjecting the contents of the charged vessel to a carbon monoxide pressure and a temperature sufficient to effect the carbonylation reaction.

In accordance with the invention 1-olefins having double bonds of the formula:

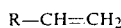

wherein R is an alkyl or hydrogen are converted, by the palladium-catalyzed addition to said double bond of carbon monoxide, oxygen and an alkanol, to produce aliphatic, dicarboxylic esters in which the double bonds have been transformed into a moiety having the formula:

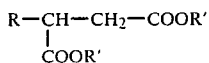

wherein R' is an alkyl group from an alkanol, such as a methyl group from methanol. The process comprises passing the aliphatic olefin, carbon monoxide and oxygen together with alkanol over a heterogenous supported palladium catalyst in the presence of cocatalysts which preferably contain a copper compound and lithium compound. The reactants and catalyst components are charged to a reaction vessel and, in the absence of water subjected to a carbon monoxide pressure and temperature for a sufficient period of time to effect the desired carbonylation reaction. In the specific use of the olefin 1-octene, the carbonylation reaction can be represented by the following equation:

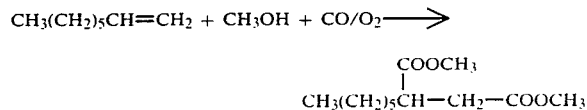

$$CH_3(CH_2)_5CH=CH_2 + CH_3OH + CO/O_2 \longrightarrow$$
$$CH_3(CH_2)_5CH\underset{|}{\overset{COOCH_3}{-}}CH_2-COOCH_3$$

with the use of propylene, the reaction can be represented by the folowing equation:

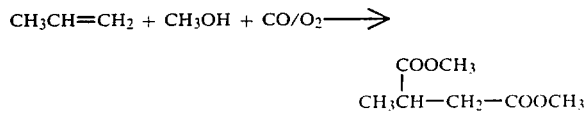

$$CH_3CH=CH_2 + CH_3OH + CO/O_2 \longrightarrow$$
$$CH_3CH\underset{|}{\overset{COOCH_3}{-}}CH_2-COOCH_3$$

Generally the reaction between the 1-olefin, carbon monoxide, oxygen and alkanol may be carried out in an autoclave or other appropriate reactor. Although the order of addition of reactants and catalyst components may vary, a general procedure is to charge the supported palladium catalyst, copper-containing cocatalyst, lithium-containing cocatalyst, 1-olefin alkanol and optional dehydrating agent to an appropriate reactor, such as a stainless-steel, magnedrive reactor, then introduce the proper amount of carbon monoxide and oxygen and increase the pressure and temperature to a desired level for an appropriate period to produce the desired aliphatic carboxylic acid derivative.

Olefins suitable for use in the present invention are simple olefins containing two to twelve atoms per molecule and having the general formula:

$$R-CH=CH_2$$

wherein R is hydrogen or a hydrocarbon radical.

Suitable olefins include ethylene, propylene, 1-butene, 1-pentene, 1-hexene, 1-heptene, 1-octene, 1-nonene, 1-decene, 1-undecene, 1-dodecene and the like. The preferred 1-olefins for the practice of this invention are 1-octene and propylene.

The alcohol coreactants used in these syntheses are aliphatic monohydric alkanols each containing one to twenty carbon atoms per molecule. Suitable aliphatic monohydric alkanols include methanol, ethanol, n-propanol, iso-propanol, tert-butanol, n-butanol, n-hexanol, n-decanol, n-dodecanol and the like. The preferred aliphatic monohydric alkanol coreactant is methanol.

As mentioned hereinabove a palladium-containing catalyst compound is employed in the process of the invention which together with the particular cocatalysts provides a catalyst system which demonstrates an increase in selectivity for carboxylic acid ester products and which allows for ease of separation, a feature which is commercially attractive and desired in the art. Thus, the palladium-compound is preferentially present wherein the palladium is bonded to an inert support material such as alumina, silica-alumina, silica gel, kaoline, keiselguhr, zirconium oxide, titania, barium carbonate, silicalite, as well as certain zeolitic silica-aluminas such as 4A-molecular sieve, and certain activated carbons. The preferred palladium-containing catalyst compound is palladium-on-activated carbon. In this case, the palladium concentration on the activated carbon support may vary from 0.1 wt. % to at least 20 wt. %. This is the range normally employed, with the preferred range being 0.5 wt. % to 5.0 wt. %.

The support may be in the form of powders, pellets, spheres, shapes and extrudates. They should also be of suitable porosity such that they may be employed in fixed or fluidized bed ratios. In the process of this invention palladium on graphite (1%) was found to be the preferred form of the catalyst. Based on converted olefin, for example, dimethyl n-hexyl-succinate was produced at 94% selectivity and 61% 1-octene conversion.

The palladium-containing precursor compound to be dispersed upon the solid support may be impregnated on said supports in the form of a bivalent palladium-containing salt, possibly as the salt of a carboxylic acid such as palladium acetate, palladium propionate, or as palladium acetylacetonate, palladium nitrate and the like. Alternately it can be added in the form of a palladium halide, such as palladium(II) chloride.

Generally, said palladium-containing catalyst system is prepared by first dissolving or slurrying the selected palladium salt, halide, etc., e.g. palladium(II) chloride, with a suitable solvent system and subsequently impregnating the selected inert support or carrier with the palladium-containing mixture. These solutions or slurries may be poured onto the carrier, or the solid carrier may be immersed in an excess of the liquid solution or slurries, with the excess being subsequently removed.

The impregnated support is then maintained at a temperature sufficient to volatize the solvent component, e.g. at a temperature between 100° C. and 500° C., to permit drying of the composite solid catalyst. A vacuum may also be applied to the catalyst in order to volatize the solvent, although use of vacuum is not essential. During this stage of the process the volatile solvent evaporates from the solid catalytic products, and the ruthenium component remains on the support.

The solvent which may be used to dissolve the palladium-containing compound prior to impregnation onto the support should be a liquid of relatively low boiling point such as, for example, about 150° C. or less. A preferable group of solvents include mineral acid solutions such as hydrochloric acid and nitric acid, carboxylic acids such as acetic acid and propionic acid, halogenated solvents like chloroform and carbon tetrachloride, ketones such as acetone and methyl isobutyl ketone, alcohols such as methanol, iso-propanol and tert-butanol, aromatics such as benzene, toluene and xylene, as well as certain heterocyclic solvents like pyridine and N-methylpyrrolidone. The choice of solvent is dependent upon the nature of the palladium-containing compound to be used for impregnation.

In accordance with this invention a copper-containing compound is used as a cocatalyst. The copper-containing cocatalyst can be added to the reactor in the form of a salt of copper such as a halide, sulfate, trifluoroacetate, nitrate, naphthalenate, hex-3-endioates or acetate. Copper salts which work include, but are not limited to copper(II) chloride, copper(II) bromide, copper(II) sulfate, cuprous chloride hydrate, copper(II) trifluoroacetate, copper(II) acetate, copper(II) triflate, copper(II) fluorosulfonate, copper(I) chloride and copper(I) sulfate.

The preferred compound is copper(II) chloride.

In the process of this invention a lithium-containing cocatalyst is used in addition to the copper-containing cocatalyst. The lithium-containing compound is selected from the group consisting of salts of lithium from the group including lithium halides, sulfates, nitrates and acetates. Examples include lithium chloride, lithium bromide, lithium iodide and lithium acetate. The preferred lithium-containing compound is lithium chloride.

Optionally a dehydrating agent may also be added to the reaction mixture in the practice of this invention. Suitable dehyrating agents that may be used during the preparation of said aliphatic carboxylic acid esters include certain acetals and ketals. These may include acetaldehyde dimethyl acetal, benzaldehyde dimethyl acetal and formaldehyde dimethyl acetal. Suitable ketals can be 2,2-dimethoxypropane, dimethoxymethane and the like. Said dehydrating agent may be used in a wide range of ratios compared with the quantity of aliphatic conjugated diene charged, but in the case of $\alpha$-olefin carbonylation, preferably 1–2 moles, or more, of dehydrating agent, such as 2,2-dimethoxypropane, are employed per mole of $\alpha$-olefins charged.

The process of the present invention can be suitably performed by introducing the oxygen, carbon monoxide and alcohol at a desired pressure into contact with the olefin, preferably 1-octene or propylene, optional dehydrating agent, the supported palladium catalyst, copper-containing cocatalyst and lithium-containing cocatalyst and heating to the desired temperature.

In general a carbon monoxide pressure of about 50 psig to about 5000 psig partial pressure and preferably about 500 psig to about 1800 psig is employed. At least stoichiometric quantities of carbon monoxide are generally employed. However, an excess of carbon monoxide may be employed, for example, particularly in continuous processes. Where a large excess of or high carbon monoxide requirements are generally utilized, a suitable recycle of the unreacted carbon monoxide may be employed.

The partial pressure of oxygen is generally selected so that the molar ratio of carbon monoxide to oxygen is in the range 1:1 to 100:1. A carbon monoxide to oxygen ratio in the range of 5:1 to 20:1 has been employed in this work for the synthesis of succinate from $\alpha$-olefins, and is considered to be the preferred range.

The reaction will proceed at temperatures above 25° C. It is generally preferred to operate the process at temperatures in the range of 80° C. to 150° C. to obtain a convenient rate of reaction with the particular olefin.

The reaction time is generally dependent upon the olefin being reacted, temperature, pressure and on the amount and type of catalyst, cocatalyst and dehydrating agent being employed. Reaction time will vary dependent on whether the process is continuous or batch and may vary from one to 15 hours. Reaction time for $\alpha$-olefins is generally about two hours.

The quantity of palladium catalyst employed in the instant invention is not critical and may vary over a wide range. In general, the carbonylation process is desirably conducted in the presence of a catalytically effective quantity of the active palladium species which gives the desired ester products in reasonable yields.

The quantity of copper-containing catalyst employed in the instant invention is not critical and may vary over a wide range. In general, the carbonylation process is desirably conducted in the presence of a catalytically effective quantity of the active copper species which along with palladium and lithium gives the desired ester products in reasonable yields. The reaction proceeds when employing concentrations of copper-containing compound of between 0.1 wt. % and 50 wt. %, with the preferred range being 0.1 wt. % to 1 wt. % and optimally about 0.5 wt. %. Higher concentrations of copper-containing compound may be used to the extent of 50 wt. %.

The quantity of lithium-containing catalyst employed in the instant invention is not critical and may vary over a wide range. In general, the carbonylation process is desirably conducted in the presence of a catalytically effective quantity of the active lithium species which along with palladium and lithium gives the desired ester products in reasonable yields. The reaction proceeds when employing concentrations of lithium-containing compound of between 0.0001 wt. % and 1.0 wt. %, with the preferred range being 0.001 wt. % to 0.1 wt. % and optimally about 0.005 wt. %. Higher concentrations of lithium-containing compound may be used to the extent of 1.0 wt. %.

The ratio of supported palladium-containing compound to copper-containing cocatalyst to lithium-containing cocatalyst is not critical. Good results are obtained using a weight ratio of Pd:Cu:Li of about 0.01:1.0:0.005.

In reacting a 1-olefin, carbon monoxide, oxygen and an alcohol in the presence of the catalyst to form an alkyl succinate, whether accomplished in continuous operations or batch experiments, the carbon monoxide may also be used in conjunction with up to 50% by volume of one or more other gases. These other gases may include one or more inert gases such as nitrogen, argon, neon and the like, or they may include gases that may, or may not, undergo reaction under CO carbonylation conditions such as carbon dioxide, hydrogen, hydrocarbons such as methane, ethane, propane and the like, ethers such as dimethyl ether, methylethyl ether and diethyl ether, and acid esters such as methyl acetate.

The 1-olefin carbonylation process disclosed herein leads to the formation of two classes of products. The primary product is the dialkyl ester, dimethyl n-hexylsuccinate or dimethyl methyl-succinate. By-products include dimethyl carbonate and $\beta$-alkoxy-carboxylate.

The benefits of the improved 1-olefin carbonylation process using the supported palladium catalyst, copper-containing cocatalyst, lithium-containing cocatalyst and optional dehydrating agent are:

(a) increased productivity and selectivity of alkyl succinate product
(b) ease of separation of said alkyl succinate from the palladium catalyst component.

The process of this invention can be conducted in a batch, semi-continuous or continuous fashion. The solid catalyst may be employed as a fixed bed. The reactor may consist of a series of catalyst beds or the catalyst may be placed in tubes with a heat exchange medium around the tubes. So as to provide certain operating advantages, the metal content of the catalyst may be varied through the reactor bed, and the reactants may be passed up-flow or down-flow through the reactor.

To ensure maximum yields of desirable products, contact between the liquid reaction mix and any iron-rich metal surfaces should be limited wherever possible during the carbonylation step. One means by which this contact can be minimized is by carrying out the olefin carbonylation reaction in a glass-lined reactor. A second, alternative method is to have the carbonylation reactor lined with some other inert materials, such as by using a silver-lined reactor, prior to effecting the diene carbonylation. Further alternatives include the use of titanium-lined pressure reactors, tantalum-lined reactors, and reactors having Hastelloy alloy or copper-nickel alloy surfaces.

Generally, operating conditions can be adjusted to optimize the formation of any desired aliphatic carboxylic diester product, and said materials may be recovered by methods well known in the art, such as filtration, distillation, fractionation, extraction and the like.

The products of this improved catalyst system have been identified by one or more of the following analytical procedures, viz, gas-liquid phase chromatography (glc), infrared (ir) mass spectrometry, nuclear magnetic resonance (nmr) and elemental analysis, or a combination of these techniques. All temperatures are in degrees centigrade and all pressures in pounds per square inch gauge (psi).

Having described the inventive process, the following examples are submitted to supply specific and illustrative embodiments.

It is to be understood these examples are illustrative and the invention is not to be limited thereby:

The following equation describes the basic reaction described in Examples I-V.

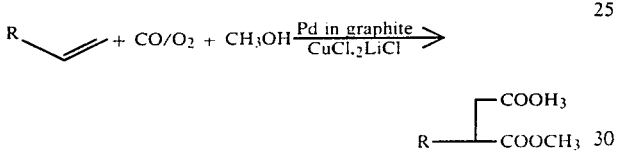

EXAMPLE I

To a 300 ml stainless-steel, magnedrive reactor was charged palladium (1.0 wt. %) on graphite (0.50 g), cuprous chloride, hydrate (0.60 g) lithium chloride (0.042 g), methanol (0.96 g) and 2,2-dimethoxypropane (20 g). The autoclave was sealed and then 10.0 g of propylene was charged and followed by pressuring CO (500 psi) and $O_2$ (100 psi). The system was heated to 100° C. and pressure was raised to 2000 psi with CO. These conditions were held for 2 hours. During the reaction process, the pressure dropped to 1700 psi. The reactor was cooled to room temperature and an off-gas sample was taken. The excess gas was vented and a brown liquid product with solid catalysts at the bottom was recovered (23.0 g). The glc analysis of liquid products and off-gas samples indicated the following product selectivities:

| | |
|---|---|
| dimethyl α-methyl-succinate | 64% |
| dimethyl carbonate | 32% |
| unknown | 4% |
| The off-gas analysis showed: | |
| carbon monoxide | 77.3% |
| carbon dioxide | .21% |
| total heavies material | 17.5% |

EXAMPLE II

The procedures of Example I were repeated except using 1-octene as the olefin substrate.

| | |
|---|---|
| dimethyl n-hexyl-succinate | 66% |
| dimethyl carbonate | 29% |
| unknown | 5% |

Dimethyl carbonate was derived from methanol and carbon monoxide. Dimethyl n-hexyl-succinate was produced from 1-octene, carbon monoxide and methanol. Based on the 1-octene reaction, 94% selectivity to dimethyl n-hexyl-succinate and 61% 1-octene conversion was realized. Dimethyl carbonate is a valuable by-product used for gasoline extender. It is also worthwhile to note that carbon dioxide in the off-gas sample was only 0.127%. The off-gas sample showed:

| | |
|---|---|
| carbon monoxide | 93.7% |
| carbon dioxide | 0.127% |
| oxygen | 0.26% |
| heavy materials | 2.6% |

EXAMPLE III

The experimental procedures were repeated except using $PdCl_2$ (0.177 g), $CuCl_2.H_2O$ (1.2 g), LiCl (0.084 g), methanol (0.96 g), 2,2-dimethoxypropane (20 g) and 10.0 g of propylene. The liquid products (33.7 g) were analyzed to be:

80% selectivity to dimethyl α-methylsuccinate
10% selectivity to dimethyl carbonate
10% selectivity to unknown materials The off-gas analysis showed:
90.7% carbon monoxide
0.19% carbon dioxide
6.8% heavy materials It should be noted that the selectivity of dimethyl α-methyl-succinate to unknown (regardless of the dimethyl carbonate formation) is different from palladium/graphite reactions (Example I).

EXAMPLE IV

The experimental procedures of Examples I-III were repeated using $PdCl_2$ (0.177 g), $CuCl_2.XH_2O$ (1.2 g), LiCl (0.084 g), methanol (20 g), propylene (10.0 g) and no 2,2-dimethoxypropane.

The similar reaction conditions gave 19.5 g of liquid product with the product selectivity, 89% to dimethyl α-methylsuccinate and 0% dimethyl carbonate.

EXAMPLE V

Example III was repeated using the same catalyst composition and reactants, except no oxygen was added. The recovered liquid components showed no products (dimethyl methylsuccinate or dimethyl carbonate). The presence of oxygen was essential.

What is claimed is:

1. A process for oxidative carbonylation of 1-olefins containing 2 to 12 carbon atoms per molecule of the formula:

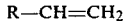

wherein R is a hydrogen or hydrocarbon radicals, by reaction with carbon monoxide and oxygen in the presence of an alkanol coreactant containing 1 to 20 carbon atoms per molecule, to form an aliphatic dicarboxylic acid ester having the formula:

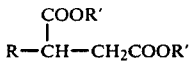

wherein R' is a alkyl group from an alkanol coreactant, said process being conducted in the presence of a hetergeneous supported palladium catalyst, a copper-containing cocatalyst, a lithium-containing cocatalyst and 2,2-dimethoxypropane, at a temperature of 80° to 150° C. and a pressure of 500 psi to 1800 psi, in order to effect the desired carbonylation reaction, and wherein the carbon monixide to oxygen ratio is from 5:1 to 20:1, the palladium catalyst is deposited on said support in a concentration range of 0.1 to 20 wt. %, the concentration of copper-containing cocatalyst is between 0.1% wt% and 50 wt. % and the concentration of lithium-containing cocatalyst is between 0.0001 wt. % and 1.0 wt. %.

2. A process according to claim 1 wherein the 1-olefin is selected from the group consisting of propylene and 1-octene, the alkanol coreactant is methanol, the supported palladium catalyst comprises 1% palladium on graphite; the copper-containing cocatalyst comprises a copper salt from the group consisting of cupric chloride, cuprous bromide and cuprous chloride hydrate; the lithium-containing cocatalyst compound comprises a lithium salt from the group consisting of lithium iodide, lithium bromide and lithium chloride; the temperature is at least 25° C.; the carbon monoxide pressure is at least 50 psi and the carbon monoxide to oxygen ratio is initially between 1:1 and 100:1 and the primary aliphatic dicarboxylic acid esters are dimethyl methylsuccinate and dimethyl n-hexyl-succinate.

3. A process according to claim 1 wherein the copper-containing cocatalyst comprises a copper salt from the group consisting of cupric chloride, cupric bromide, cupric iodide and cuprous chloride hydrate.

4. A process according to claim 1 wherein the lithium-containing cocatalyst comprises lithium chloride.

5. A process according to claim 1 wherein the support for the palladium catalyst is graphite.

6. A process according to claim 2 wherein said dimethyl hexylsuccinate product is separated from said palladium catalyst system by filtration.

* * * * *

UNITED STATES PATENT AND TRADEMARK OFFICE
CERTIFICATE OF CORRECTION

PATENT NO. : 4,554,374

DATED : November 19, 1985

INVENTOR(S) : Jiang-Jen Lin

It is certified that error appears in the above-identified patent and that said Letters Patent is hereby corrected as shown below:

Column 10, Claim 2, line 1, delete "compound".

Signed and Sealed this

Eighteenth Day of February 1986

[SEAL]

Attest:

DONALD J. QUIGG

Attesting Officer

Commissioner of Patents and Trademarks